United States Patent [19]
Yoshida

[11] Patent Number: 4,875,265
[45] Date of Patent: Oct. 24, 1989

[54] INJECTION NEEDLE-DETACHING DEVICE

[75] Inventor: Toshiki Yoshida, Osaka, Japan

[73] Assignee: Nissho Corporation, Osaka, Japan

[21] Appl. No.: 267,480

[22] Filed: Nov. 4, 1988

[30] Foreign Application Priority Data

Dec. 14, 1987 [JP] Japan ................................ 62-189702

[51] Int. Cl.⁴ .............................................. B65D 25/00
[52] U.S. Cl. ........................................ 29/240; 206/366
[58] Field of Search ...................... 29/240, 240.5, 239, 29/280, 282; 206/365, 366, 370

[56] References Cited

U.S. PATENT DOCUMENTS

| | | |
|---|---|---|
| 4,255,996 | 3/1981 | Choksi et al. . |
| 4,375,849 | 3/1983 | Hanifl . |
| 4,466,538 | 8/1984 | Gianni . |
| 4,807,344 | 2/1989 | Kelson et al. ........................... 29/240 |

FOREIGN PATENT DOCUMENTS

| | | |
|---|---|---|
| 0136392 | 4/1985 | European Pat. Off. . |
| 8614635 | 10/1986 | Fed. Rep. of Germany . |
| 8708179 | 10/1987 | Fed. Rep. of Germany . |
| 60-54361 | 3/1985 | Japan . |
| 8200412 | 2/1982 | PCT Int'l Appl. . |
| 8800067 | 1/1988 | PCT Int'l Appl. . |
| 79/00239 | 2/1979 | World Int. Prop. O. . |

Primary Examiner—Robert C. Watson
Attorney, Agent, or Firm—Armstrong, Nikaido, Marmelstein, Kubovcik & Murray

[57] ABSTRACT

A device for detaching an injection needle from a syringe comprising: a plate-like member, a first opening provided in the plate-like member for inserting an injection needle attached to a syringe, a first needle-detaching means for detaching a slip type needle, said first means comprising a second opening extending laterally from said first opening, and a sliding portion provided on each of both sides of said second opening, each sliding portion having a wedge-like shape, and a second needle-detaching means for a screw type needle, said second means comprising a third opening extending laterally from said first opening, said third opening having a portion having such a size that the hub of said needle is capable of being inserted thereinto, said portion being provided with a projection for preventing the hub of said needle from turning when the syringe is turned. By using the device, both the slip type needle and the screw type needle can be detached from the syringe with safety without touching the needle with finger.

4 Claims, 5 Drawing Sheets

INJECTION NEEDLE-DETACHING DEVICE

BACKGROUND OF THE INVENTION

The present invention relates to a device for detaching an injection needle from a syringe. More particularly, the present invention relates to a device for detaching a used needle from a syringe with safety without touching the needle with finger.

There are two kinds of injection needles with respect to the manner of attaching the needle to a syringe. The one is a slip type wherein a needle has a hub with a plain inner surface and the hub is simply forced to be put on the nozzle portion of a syringe that has a plain outer surface. The other is a screw type wherein a needle has a hub having a female thread on the inner surface thereof and the hub is threaded onto the nozzle portion of a syringe that has a male thread on the outer surface thereof.

Conventionally, the injection needle was detached from the syringe by simply pulling out it or by unthreading it with holding the hub thereof with fingers. At the first glance, such detaching operation appears to be easy. However, an accident that finger is injured with the needle inevitably happens when the same person repeats the needle-detaching operation several tens times or more a day.

Recently diseases infectious through blood such as viral hepatitis and acquired immuno-deficiency syndrome (AIDS) have increased rapidly. For the reason, it is important that persons who are engaged in test for the diseases and treatment of the diseases get out of direct touch with the blood of patients.

However, when a used needle is detached from a syringe in the conventional manner, there is a great possibility that a person gets hurt in the finger with the needle and the blood attached to the needle is entered into the body of the person through the wound so that the person is infected with the above-mentioned disease.

Accordingly, there is a demand for a means of detaching the needle from the syringe without touching the needle with finger.

With respect to a blood-drawing needle which generally has two needles extending in the opposed directions from the hub, a needle disposal system including a disposable bottle having a cap in compliance with the demand is proposed, as disclosed in U.S. Pat. No. 4,466,538. The cap is provided with a slot which has a large width at one end and is narrowed toward the other end and one side of the slot in the narrow portion is contoured to define a serrated edge. The blood-drawing needle attached to a syringe is inserted into the wide portion of the slot and then moved toward the narrow portion, thereby catching the hub of the needle between both the side walls of the narrow portion. When the syringe is turned in such a state, the engagement between the syringe and the needle is loosened, so that the needle falls into the bottle.

However, the needle disposable system has a drawback that since the hub of the needle is firmly caught between the side walls of the slot when the syringe is turned, the needle tends to remain in that position without falling into the bottle and the operator gets hurt in the finger with the needle when he touches the needle to remove the caught needle.

It is an object of the present invention to provide a needle-detaching device capable of detaching a used needle from a syringe with an easy operation without touching the needle with finger.

Another object of the invention is to provide a needle-detaching device having both a needle-detaching function for a slip type needle and a needle-detaching function for a screw type needle.

These and other objects of the present invention will become apparent from the description hereinafter.

SUMMARY OF THE INVENTION

The present invention provides a device for detaching an injection needle from a syringe comprising:

a plate-like member, a first opening provided in the plate-like member for inserting an injection needle attached to a syringe, a first needle-detaching means for detaching a slip type needle, and a second needle-detaching means for detaching a screw type needle, said first opening having a size larger than the largest part of said needle, said first needle-detaching means comprising a second opening extending laterally from said first opening, and a sliding portion provided on each of both sides of said second opening, said second opening having a width larger than the diameter of the nozzle of said syringe and smaller than the diameter of the hub of said needle, each of said sliding portion having a side wall defining said second opening, each of said side walls having, at the entrance of the second opening from said first opening, a thickness smaller than a distance between the root of the nozzle of said syringe and the bottom end of the hub of said needle when the needle is being attached to said syringe, each of said side walls being made gradually thicker toward the closed end of said second opening, the maximum thickness of each of said side walls being larger than said distance, said second needle-detaching means comprising a third opening extending laterally from said first opening, said third opening having a portion having such a size that the hub of said needle is capable of being inserted thereinto, said portion being provided with a projection for preventing the hub of said needle from turning when the syringe is turned.

DETAILED DESCRIPTION

First a syringe and an injection needle are explained in order to give a better understanding of the description hereinafter.

Figure 10:
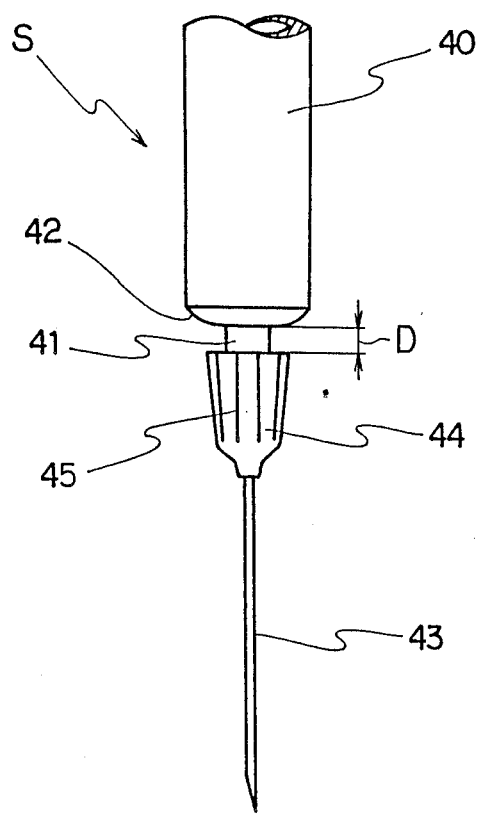
FIG. 10 is an explanatory view showing a syringe.

Referring to FIG. 10, the numeral 40 indicates a barrel of a syringe S. The syringe barrel 40 has a nozzle 41 at one end. The numeral 42 indicates a shoulder portion at the root of the nozzle 41. The numeral 43 indicates an injection needle and the injection needle 43 extends from a hub 44.

The above-mentioned elements are fundamental elements common to both a slip type needle and a screw type needle. In the case of the slip type needle, the hub 44 has a cavity with a plain inner surface and the corresponding nozzle 41 also has a plain outer surface. In the case of the screw type needle, the hub 44 has an inner surface provided with a female thread and the corresponding nozzle 41 has an outer surface provided with a male thread. Plural ribs 45 are provided on the outer surface of the hub 44 in the longitudinal direction thereof for the purpose of providing a moderate fitting strength between the hub 44 and a protector for the needle 43.

In the present invention, the term "syringe" is intended to comprehend a blood-collecting tube in addition to a normal syringe. Also the term "injection needle" is intended to comprehend a blood-drawing needle in addition to a normal injection needle.

The device of the present invention has both the function of detaching a slip type needle and the function of detaching a screw type needle.

An example of the needle-detaching device of the present invention will be explained by referring to FIGS. 1 to 9.

Figure 1:
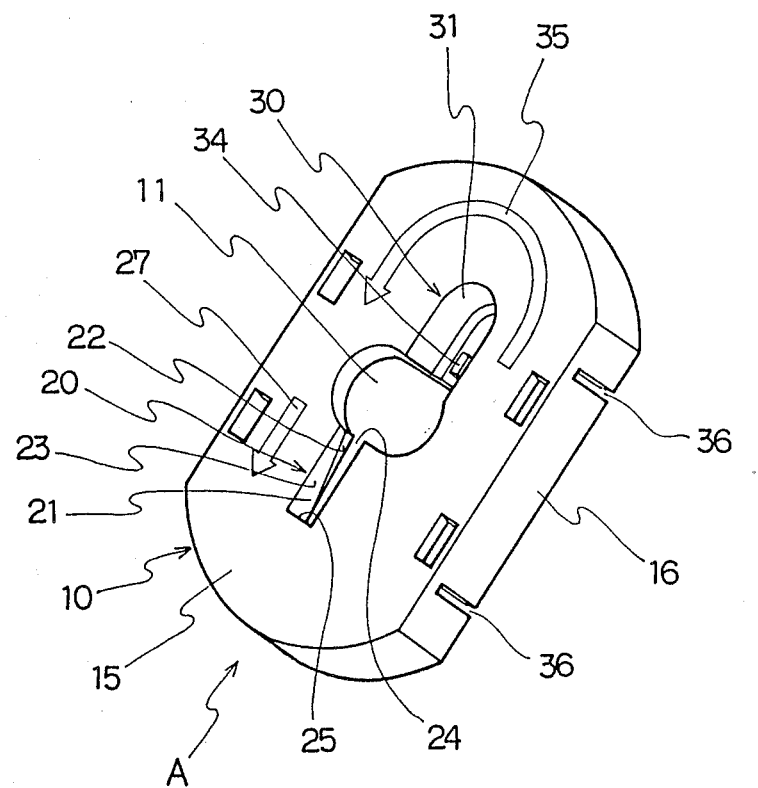
FIG. 1 is a perspective view showing an example of the needle-detaching device of the present invention.
Figure 2:
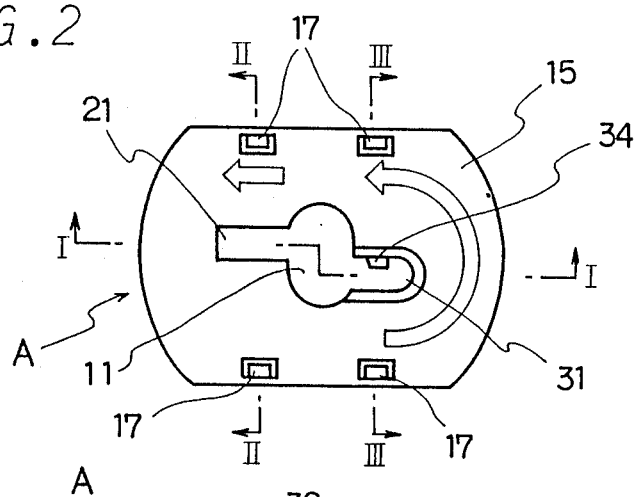
FIG. 2 is a plan view showing the device illustrated in FIG. 1.
Figure 3:
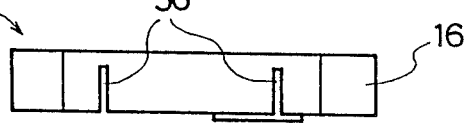
FIG. 3 is an elevational view showing the device illustrated in FIG. 1.
Figure 4:
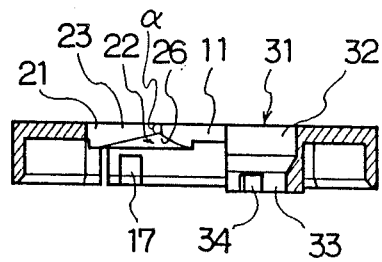
FIG. 4 is a sectional view taken along the line I—I in FIG. 2.
Figure 5:
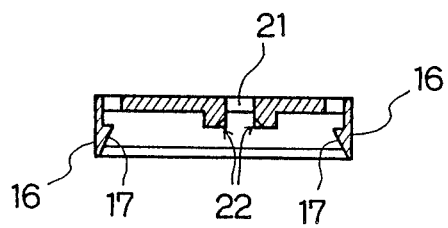
FIG. 5 is a sectional view taken along the line II—II in FIG. 2.
Figure 6:
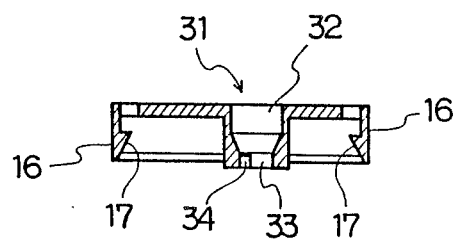
FIG. 6 is a sectional view taken along the line III—III in FIG. 2.

FIG. 1 illustrates a needle-detaching device A. The needle-detaching device A comprises a plate-like member 10, a first opening 11 for inserting the lower portion of a syringe S, the first opening 11 being provided in the central portion of the member 10, a first needle-detaching means 20 for a slip type needle and a second needle-detaching means 30 for a screw type needle, the means 20 and the means 30 being provided on the opposed sides of the first opening 10.

Figure 7:
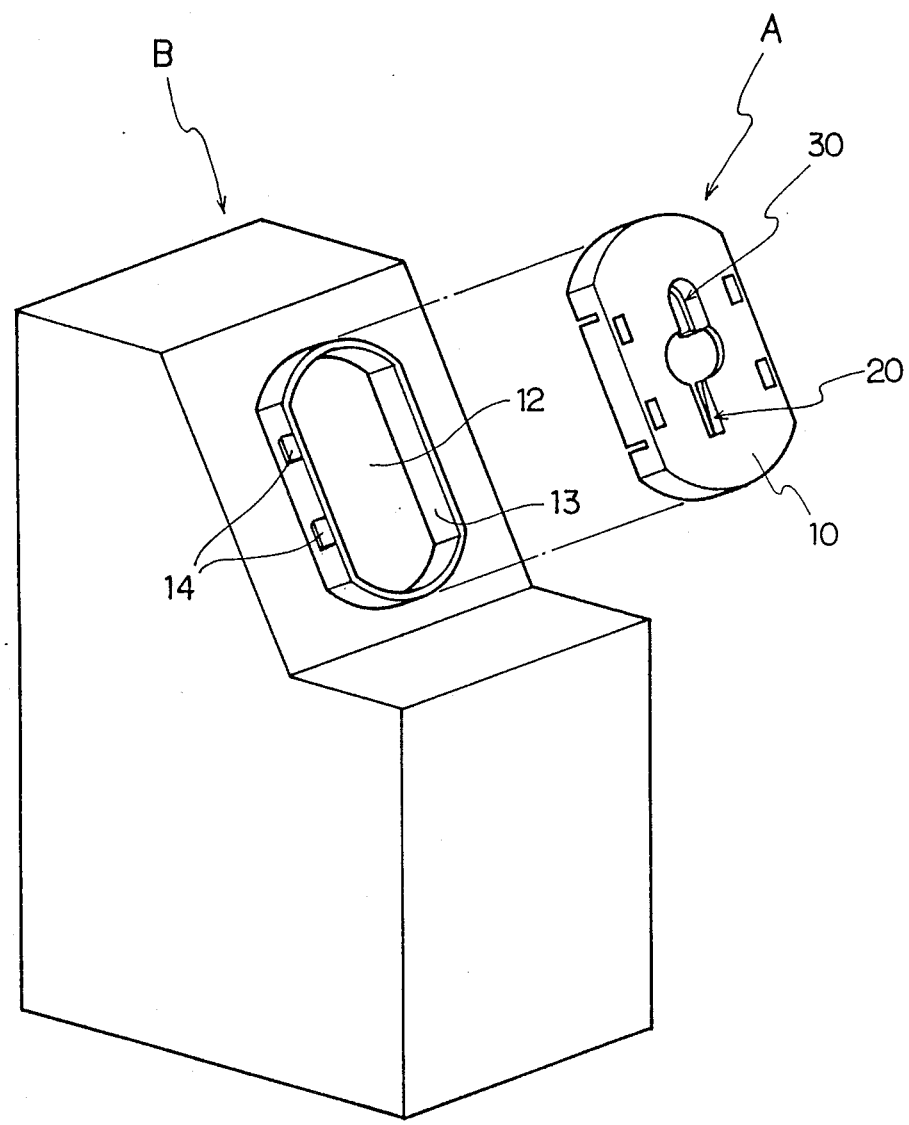
FIG. 7 is a perspective view showing the needle-detaching device illustrated in FIG. 1 and a container on which the needle-detaching device is to be mounted.

The needle-detaching device A, when being used, is mounted on a container B for containing used needles, as shown in FIG. 7. The shape of the container B is not particularly limited. An opening 12 is provided in a part of container B, and a rib 13 and engaging projections 14 are provided in the periphery of the opening 12 to install the needle-detaching device A.

The construction of the needle-detaching device A will be explained in detail by referring to FIGS. 1 to 6.

The plate-like member 10 comprises an upper plate 15 and a skirt 16 provided in the periphery of the upper plate 15. Usually the plate-like member 10 is integrally formed from a synthetic resin such as polyethylene, polypropyrene, acrylonitril-butadienestyrene copolymer, polycarbonate or polyester.

The upper plate 15 has an opening 11 provided in the central portion thereof. The opening 11 is nearly elliptical in shape and has such a size that the hub 44 of the needle 43 can be freely inserted thereinto. When the needle 43 is covered with a protector, the opening 11 preferably has a size larger than the diameter of the protector so that the needle 43 covered with the protector can be detached from the syringe S.

The first needle detaching means 20 comprises a second opening 21 extending from and communicating with the first opening 11, and a sliding portion 22 provided on each of both sides of the second opening 21.

Each sliding portion 22 has a side wall 23 defining the second opening 21. Each sliding portion 22 is formed so that the side wall 23 is the thinnest at the entrance 24 of the second opening 21 and made gradually thicker toward the closed end 25 of the second opening 21.

The width of the second opening 21 is somewhat larger than the diameter of the nozzle 41 and must be smaller than that of the barrel 40 and that of the hub 44.

The thickness of the thinnest part of the side wall 23, i.e. the thickness of the side wall 23 at the entrance 24, must be smaller than the distance D between the root of the nozzle 41 and the bottom surface of the hub 44 when the hub 44 is firmly put on the nozzle 41. The thickest part of the side wall 23 must have a thickness sufficient to detach the hub 44 from the nozzle 41. The thickest part of the side wall 23 has a thickness larger than the distance D between the root of the nozzle 41 and the bottom surface of the hub 44 when the hub 44 is firmly put on the nozzle 41. The sliding surface 26 of the sliding portion 22 on the rear side of the plate 15, on which the bottom surface of the hub 44 slides, is inclined both in the direction of the first opening 11 and in the direction of the second opening 21.

Further the angle $\alpha$ between both edge lines of the side wall 23 in the longitudinal direction of the second opening 21 is preferably from 5° to 45°, more preferably from 15° to 30°, to facilitate a smooth removal of the hub 44 from the nozzle 41.

Preferably an arrow mark 27 for indicating the movement direction of the syringe S is provided on a side of the second opening 21 on the plate 15.

The second needle-detaching means 30 contains a third opening 31 having a U shape in plain. The third opening 31 comprises a big-sized portion 32 having such a size that the hub 44 of the needle 43 is easily inserted thereinto and a small-sized portion 33 extending vertically from the big-sized portion 32 and having such a size that only the tip portion of the hub 44 can be inserted thereinto. The small-sized portion 33 has a projection 34 formed on a part of the side wall thereof. The projection 34 serves to prevent the rotation of the hub 44 due to the engagement of the projection 34 with the rib 45 of the hub 44.

The reason why the small-sized portion 33 is provided under the big-sized portion 32 and the projection 34 is provided in the small-sized portion 33 is that the center of gravity of the needle 43 when being inserted in the third opening 31 is positioned under the upper surface of the plate 15, thereby preventing the detached needle 43 from falling out of the device A.

Preferably an arrow mark 35 for indicating the direction of the rotation of the syringe S is provided around the third opening 31.

The skirt 16 has two slits 36, 36 on each of the opposed sides thereof so that a part of the skirt 16 between the two slits 36, 36 is made somewhat flexible. The part of the skirt 16 between the two slits 36, 36 has engaging projections 17 on the rear surface thereof. The engaging projections 17 are engaged with the engaging projections 14 of the container B. The number of the projections 17 is not particularly limited. In this example, two projections on each side of the skirt 16, four projections in total, are formed. The device A is installed to the container B by resiliently engaging the projections 14 of the container B with the projections 17 of the device A.

The operation of detaching an injection needle from a syringe by means of the device A is explained.

Figure 8:
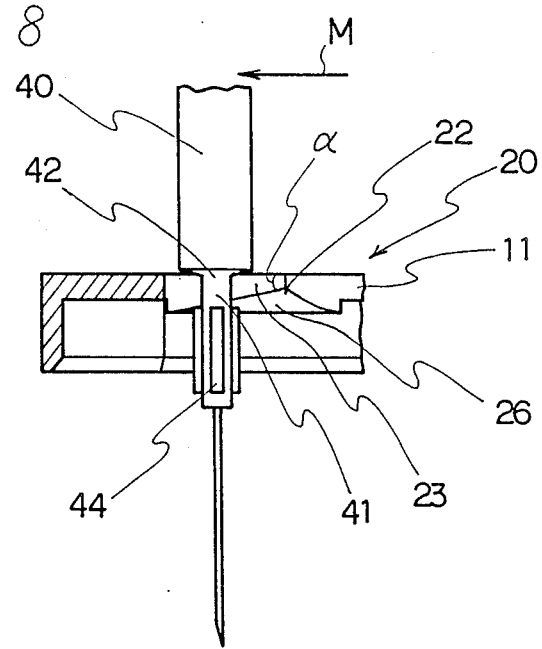
FIG. 8 is an explanatory view showing the needle-detaching operation with respect to a slip type needle.

FIG. 8 illustrates the operation of detaching a slip type needle. The lower portion of the injection barrel 40 is inserted into the first opening 11 and put on the entrance 24 of the second opening 21. The nozzle 41 is inserted between both side walls 23, 23 and the shoulder portion 42 is brought into contact with the upper surfaces of the sliding portions 22 and the bottom surface of the hub 44 is brought into contact with the sliding surfaces 26, 26. When the injection barrel 40 is moved in the direction of the arrow M, the hub 44 is pushed downward because of increasing thickness of each sliding portion 22, thereby separating the hub 44 from the nozzle 41. The device A is preferably installed to the container B so that the barrel 40 can be moved downward as shown in FIG. 7 because it is easy to apply force on the barrel 40.

Figure 9:
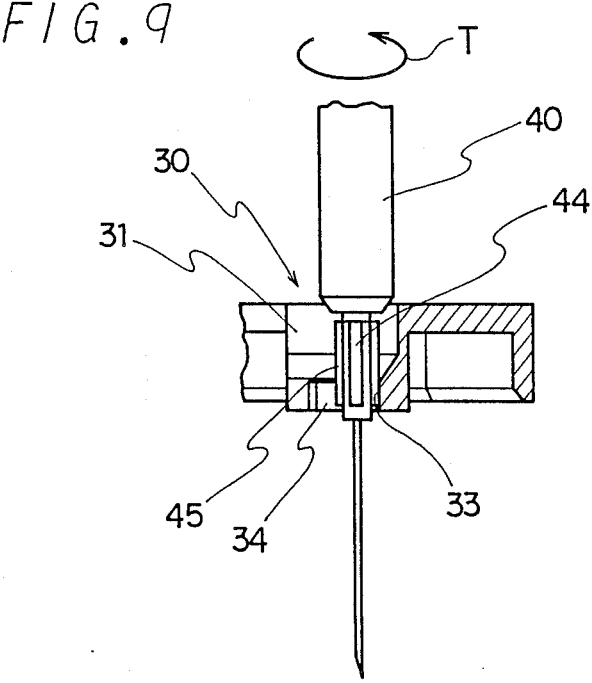
FIG. 9 is an explanatory view showing the needle-detaching operation with respect to a screw type needle.

FIG. 9 illustrates the operation of detaching a screw type needle. The lower portion of the injection barrel 40 is inserted downward into the third opening 30 and the hub 44 is inserted into the small-sized portion 33, engaging the rib 45 of the hub 44 with the projection 34. When the barrel 40 is turned several turns in the direction of the arrow T in such a state, the needle 43 is loosened and detached from the nozzle 41. Alternatively the barrel 40 is turned about one turn, followed by movement toward the first opening 11. In that case, the hub 44 is turned in such a manner that it crosses the projection 34, whereby the hub 44 is unthreaded and detached from the nozzle 41.

As described above, by using the needle-detaching device A, an injection needle can be detached without touching the tip of the injection needle with finger. Further an injection needle can be detached by using only the device A regardless of whether the needle is a slip type needle or a screw type needle.

The device A of the above-mentioned example is nearly elliptical in plane shape. However the device A may be circular in plane shape. In that case, the skirt 16 can be designed so that it can be installed to a container by fitting or screwing. The device A having such a skirt 16 can be installed to a suitable bottle as the container B. In that case, no individually designed container is needed.

By using the needle-detaching device A of the present invention, an injection needle can be readily detached with safety without injuring the finger. Further detachment of both a slip type needle and a screw type needle can be effected by using only the device A.

In addition to the elements used in the Examples, other elements can be used in the Examples as set forth in the specification and the drawings to obtain substantially the same results.

What is claimed is:

1. A device for detaching an injection needle from a syringe comprising:
    a plate-like member,
    a first opening provided in the plate-like member for inserting an injection needle attached to a syringe,
    a first needle-detaching means for detaching a slip type needle, and
    a second needle-detaching means for detaching a screw type needle,
    said first opening having a size larger than the largest part of said needle,
    said first needle-detaching means comprising a second opening extending laterally from said first opening, and a sliding portion provided on each of both sides of said second opening,
    said second opening having a width larger than the diameter of the nozzle of said syringe and smaller than the diameter of the hub of said needle,
    each of said sliding portion having a side wall defining said second opening,
    each of said side walls having, at the entrance of the second opening from said first opening, a thickness smaller than a distance between the root of the nozzle of said syringe and the bottom end of the hub of said needle when the needle is being attached to said syringe, each of said side walls being made gradually thicker toward the closed end of said second opening, the maximum thickness of each of said side walls being larger than said distance,
    said second needle-detaching means comprising a third opening extending laterally from said first opening,
    said third opening having a portion having such a size that the hub of said needle is capable of being inserted thereinto, said portion being provided with a projection for preventing the hub of said needle from turning when the syringe is turned.

2. The device of claim 1, in which the angle between both edge lines of each side wall in the longitudinal direction of said second opening is from 5° to 45°.

3. The device of claim 1, in which said third opening comprises a big-sized portion having such a size that the hub of the needle is smoothly inserted thereinto and a small-sized portion extending vertically from the big-sized portion and having such a size that only the tip portion of the hub is capable of being inserted thereinto, said projection being provided on a part of the side wall of the small-sized portion.

4. The device of claim 1, in which said plate-like member is designed so that it is detachably installed to a container for containing removed needles.

* * * * *